United States Patent [19]

Larson et al.

[11] Patent Number: 4,696,769

[45] Date of Patent: Sep. 29, 1987

[54] METHOD AND BINDER FOR THE MANUFACTURE OF NUCLEAR FUEL PELLETS, AND THE PRODUCT

[75] Inventors: Richard I. Larson, Wilmington; Richard P. Ringle, Scotts Hill; John D. Connolly, Jr.; Timothy J. Gallivan, both of Wilmington, all of N.C.

[73] Assignee: General Electric Company, San Jose, Calif.

[21] Appl. No.: 744,962

[22] Filed: Jun. 17, 1985

Related U.S. Application Data

[63] Continuation of Ser. No. 517,588, Jul. 27, 1983, abandoned.

[51] Int. Cl.$^4$ .................... G21C 21/00; C09K 11/04; C07F 5/00
[52] U.S. Cl. .................................. 252/638; 252/639; 264/0.5; 534/13
[58] Field of Search ................ 264/0.5; 252/638, 639; 534/13

[56] References Cited

U.S. PATENT DOCUMENTS

| | | | |
|---|---|---|---|
| 4,061,700 | 12/1977 | Gallivan | 264/0.5 |
| 4,427,579 | 1/1984 | Gaines, Jr. et al. | 264/0.5 X |
| 4,432,915 | 2/1984 | Gallivan | 264/0.5 |
| 4,522,769 | 6/1985 | Connolly, Jr. et al. | 264/0.5 |

Primary Examiner—John F. Terapane
Assistant Examiner—Virginia B. Caress
Attorney, Agent, or Firm—Robert R. Schroeder; Raymond G. Simkins

[57] ABSTRACT

A method and binder composition for prolonging the induced plasticity of a particulate ceramic material admixture comprising uranium dioxide and a fugitive binder, and product thereof, for subsequent compaction by compression molding in the manufacture of nuclear fuel pellets. The fugitive binder comprises a reaction product of an amine carbonate or amine carbamate and ammonium oxalate reacted with uranium dioxide at a temperature of at least 65° C. The uranyl oxalate-carbonate reaction product has the composition of $(UO_2)(CO_3)(C_2O_4) \cdot 2H_2O) \cdot 2H_2O$.

21 Claims, No Drawings

METHOD AND BINDER FOR THE MANUFACTURE OF NUCLEAR FUEL PELLETS, AND THE PRODUCT

This is a continuation of application Ser. No. 517,588, filed 27 July 1983, now abandoned.

FIELD OF THE INVENTION

This invention relates generally to the ceramic art and the formation of sintered bodies from particulate oxide materials. It is particularly concerned with a process for producing consolidated units of particulate ceramic materials, including the compressing of such particles into coherent and handleable compacts for subsequent sintering to integrated bodies. The invention is specifically directed to the manufacture of nuclear fuel pellets or units from particulate materials containing uranium dioxide.

CROSS-REFERENCE

This invention is generally related to that disclosed and claimed in U.S. patent application Ser. No. 331,492 filed Dec. 17, 1981, in the names of George L. Gaines, Jr., Patricia A. Piacente, William J. Ward III, Peter C. Smith, Timothy J. Gallivan, and Harry M. Laska, U.S. Pat. No. 4,427,579, issued Jan. 24, 1984, and to Ser. No. 273,900 filed June 15, 1981, in the names of George L. Gaines, Jr. and William J. Ward III, U.S. Pat. No. 4,389,341, issued June 21, 1983. Both of said applications are assigned to the same assignee as this application, and are incorporated herein by reference.

BACKGROUND OF THE INVENTION

Fissionable nuclear fuel comprises a variety of compositions and forms of fissionable materials, including ceramic compounds of uranium, plutonium and thorium. Fuel compounds for commercial power generating reactors typically comprise oxides of uranium, plutonium and thorium, and mixtures thereof. The generally most suitable and commonly used fuel for such commercial nuclear reactors is uranium dioxide. Such commercial fuel materials can be combined with minor amounts of other ingredients, including neutron flux controlling additives such as gadolinium.

Commercially produced uranium dioxide is a fine, fairly porous powder, a form which is not suitable as such for use as fuel in commercial reactors. A number of means have been developed and used to convert powdered uranium dioxide into a form suitable for use as a fuel in power generating nuclear reactors. One commonly used technique has been to sinter appropriately sized bodies of the powdered uranium dioxide material at high temperatures to develop strong diffusion bonds between the individual power particles.

However, the sintering technique requires a preliminary compressing of the loose powder into a shaped, and self-retaining compacted body of particles of sufficient strength and integrity to survive handling and the sintering procedure. The operation of compressing fine particles into a body or coherent compact with acceptable low reject levels, and with the strength and uniformity for enduring subsequent handling and firing and grinding to size has been a subject of considerable concern and investigation in the nuclear fuel industry.

Conventional organic or plastic binders commonly used in powder fabrication have been considered to be unsuitable in nuclear fuel processing operations. Entrainment of any binder residues such as carbon within the sintered nuclear fuel product is unacceptable in reactor service. Moreover, the presence of any organic binder among the particles inhibits the formation during sintering of strong diffusion bonds between the particles, and adversely affects the density of the sintered product. The complete removal of binders, or their decomposition products, prior to sintering is especially difficult, and usually requires a costly additional operation in the fuel manufacture.

Accordingly, a common method has been to die press uranium dioxide powder into approximately sized "green" (unfired) compacts without the assistance of any binder. This approach however has resulted in very costly high rates of rejects and scrap material recycling because of the weakness of such green, binder-free compacts of powder.

U.S. Pat. No. 4,061,700, issued Dec. 6, 1977, to Gallivan, and assigned to the same assignee as this application, discloses a distinctive group of fugitive binders that improved the production of sintered pellets of particulate nuclear fuel materials for nuclear reactors. The fugitive binders of this patent function without contaminating the resulting fuel product, and they permit the formation of effective bonds between sintered particles during firing without deleteriously affecting the desired porosity of the fused pellet.

The disclosure of the said U.S. Pat. No. 4,061,700, and of U.S. Pat. Nos. 3,803,273; 3,923,933; 4,389,341; 4,427,579; and 3,927,154, also assigned to the same assignee as the instant application, and relating to significant aspects in the subject field of producing nuclear fuel pellets from particulate fissionable ceramic material for reactor service, are all incorporated herein by reference.

The prior art techniques or means such as disclosed in U.S. Pat. No. 4,061,700, have been found wanting in some conditions and circumstances. For instance it has been observed that the fugitive binders of the aforesaid patent do not provide consistent results as to pellet strength and integrity irrespective of the blending conditions and particle characteristics of the uranium dioxide powder. Specifically the severity of agitation in blending, relative humidity and temperature, and duration of storage, as well as the uranium dioxide powder properties such as size, surface area and moisture content are all factors that apparently can detract from the uniformity of the physical attributes provided by such fugitive binders. These shortcomings are more evident when higher rates of die pressing are applied.

More effective and practical fugitive binder systems have been provided in this art for imparting improved plasticity to such particulate ceramic materials for their consolidation into coherent compacts with a minimum of rejects over a wide range of production rates, including high speed pressing with continuous rotary presses. Examples of such improved fugitive binder systems comprise the amine-type binder of the aforesaid applications Ser. Nos. 331,492 and 273,900, now U.S. Pat. No. 4,427,579 and No. 4,389,341.

However, it has been found that the improved plastic properties provided by such binder systems may not be lasting in that they exhibit a tendency to diminish over prolonged periods of time following their blending with nuclear fuel material. Thus, it is not feasible to store or retain over extended periods molding compositions comprising admixtures of particulate ceramic materials and such amine binders. This shortcoming imposes an impediment to production scheduling and any shipping which entail prolonged periods.

Experience with the amine carbamate-type of fugitive binder admixed with uranium dioxide-containing nuclear fuel material indicates that exposure to moisture is a likely factor in diminishing the initially effective plasticity provided by such binders. Moreover, elevated temperatures have also been found to reduce the plastic properties of these admixtures. Thus, over long periods of time, molding combinations of particulate ceramic materials containing uranium dioxide and such amines tend to lose their stability by becoming more brittle and less amenable to rapid compression molding, with the result of a high rate of rejects during compression molding.

SUMMARY OF THE INVENTION

This invention comprises a method of producing coherent compacts from particulate ceramic material wherein the ceramic material is rendered and retained more plastic, or less brittle, for compression molding over extended periods of time. Thus the invention entails a process comprising a combination of specified ingredients employed together, including the essential combination providing the fugitive binder for the compression molding step.

OBJECTS OF THE INVENTION

It is a primary object of this invention to provide a method and fugitive binder compositions for rendering particulate ceramic material more amenable to compression molding over extended periods of time, and the product thereof.

It is another object of this invention to provide means for overcoming the brittle nature of ceramic particles and to impart enduring plasticity to such a materials whereby it can be compression molded under essentially all compacting conditions and at high rates with a lower and feasible level of rejects for extended periods.

A further object of this invention is to extend the time for compression molding of particulate ceramic materials comprising uranium dioxide powder and uranyl oxalate-carbonate composition fugitive binders into coherent compacts, and to preserve the plastic properties and molding amenability thereof.

A still further object of this invention is to provide a method of producing nuclear fuel pellets comprising uranium dioxide from particulate ceramic material wherein a combination of the particulate ceramic and binder, and its properties are stable and can be compression molded to a coherent compact at fast rates with minimal rejects due to fractures over long periods of time following the combining of said ingredients.

Another object of this invention is to provide a compression moldable particulate material comprising uranium dioxide which has lasting plasticity and is amenable to compression molding over prolonged periods of time.

DETAILED DESCRIPTION OF THE INVENTION

This invention comprises a method for producing a fissionable nuclear fuel product in pellet form from particulate ceramic material utilizing a fugitive binder system which is subsequently removed during the sintering operation. The method relates to compression molding of particulate ceramic material containing uranium dioxide powder combined with a unique fugitive binder composition of the invention to form coherent compacts of apt dimensions, and thereafter sintering the compacts to produce integrated bodies of fissionable nuclear fuel suitable for use in nuclear reactors.

The particulate fissionable nuclear fuel materials for use in this invention comprise various materials used as nuclear fuels for nuclear reactors, including ceramic compounds such as oxides of uranium, plutonium and thorium. Preferred fuel compounds consist of uranium oxide, plutonium oxide, thorium oxide, and mixtures thereof.

The particulate nuclear fuel material in the practice of the invention can also include various additives such as high neutron absorbing materials comprising gadolinium to moderate neutron flux densities.

Fugitive binder systems suitable for use in the practice of this invention include the amine-containing compounds disclosed and claimed in the above identified applications for patent Ser. Nos. 331,492 and 273,900. These consist of amine compounds selected from the group consisting of amine carbonates and amine carbamates such as carbonates or carbamates of ethylene diamine; monomethylene; 3,3 diaminodipropylamine; 1,3 diaminopropane; 1,6 diaminohexane; n butyl amine; diethylene triamine; and 1,7 diaminoheptane.

In this invention the above amine-containing compounds and ammonium oxalate are added to the particulate ceramic fuel material containing uranium dioxide. The combined binder ingredients and product thereof are then blended substantially uniformly through the particulate material.

According to this invention, the improved fugitive binder system providing lasting plasticity to the particulate ceramic nuclear fuel material comprising uranium dioxide which endures adverse conditions over prolonged periods, is prepared as follows.

Ammonium oxalate, which is of low solubility in water, is added to uranium dioxide powder together with an aqueous solution of an amine. Hydrolysis of the amine compound increases the pH of the solution which facilitates dissolution of the ammonium oxalate with rapid evolution of ammonia gas at elevated temperatures. Thus, following a typically brief period upon combining the ammonium oxalate with the amine in aqueous solution of for example about 10 to 30 minutes or longer, and a temperature of at least about 65° C., for said binder forming ingredients to interact, they form a reaction product providing a fugitive binder. The combined and interacted ingredients including the formed binder composition are dried to remove excessive moisture by any suitable means such as the application of heated nitrogen gas moderately increased in temperature up to about 150° C.

This unique binder system which imparts a high degree of plasticity, has been found to be stable and highly resistant to reaction with water and in turn deterioration. Moreover it has also been found to be stable at relatively elevated temperatures of up to about 85° C., over extended periods. At higher temperatures of about 200° C. it aptly decomposes for its effective elimination in the subsequent sintering step. Accordingly, the unique binder system of this invention is not degraded when blends thereof with particulate nuclear fuel material are stored or otherwise retained for long periods of time, even under adverse conditions of high humidity and high temperature.

Proportions of such binder forming ingredients for the compositions of this invention preferably comprise the use of an amine compound identified above in amounts of from about 0.5% to about 7% by weight based upon the weight of the nuclear fuel material. The ammonium oxalate is included in amounts of from about 0.25% to about 4% by weight of the nuclear fuel material. Quantities of such binder ingredients in excess of the above upper amounts generally do not provide a proportionally commensurate benefit in bonding capacity, and may introduce unwanted effects that compromise any advantages or the costs of including greater amounts of these ingredients.

As noted hereinbefore, the amine compound is dissolved in water to facilitate the interaction of the less soluble ammonium oxalate with the amine. Amine water solutions of any practical concentration for achieving the interaction and addition to the particulate ceramic nuclear fuel can be employed. For instance excesses of water which must be removed later in the operation are not expedient. However, amine compound water solutions of, for example, about 40% to about 50% solids are generally appropriate. Excessive water is removed following the reaction period. Suitable means for water removal comprise passing nitrogen gas at a temperature of up to about 150° C. through the particulate mixture of ingredients and their reaction product for a typical period of about 20 to about 60 minutes, or longer if appropriate.

A binder system prepared of the foregoing ammonium oxalate and amine compound in solution in accordance with this invention is blended uniformly with the particulate ceramic nuclear fuel material containing ceramic dioxide, and the resultant mixture can thereafter be compressed into a coherent compact of suitable dimensions pursuant to the procedures and means of the art. The method of this invention imparts a high of plasticity and enables the prompt use, or long delayed use, such as resulting from extended storage or shipment, of the blend of fugitive binder and particulate fuel material. Moreover, the enduring plasticity attributable to the invention is adequate for the effective use of the blends in high speed, continuous production rotary press devices and operations for long periods after preparing the blend to provide unfired coherent compacts.

The "green" (unfired) coherent compacts thus formed are then sintered in accordance with the practices and procedures of the art to expel binder material and integrate the ceramic particles into a uniform and continuous body. The sintered product, typically in the form of a pellet, is thereafter ground to specified dimensions for its designated service.

Blending of the added binder can be effected with any appropriate "dry" mixing apparatus including low shear blenders such as fluidized bed, slab and ribbon blenders, and high shear or intensive blenders such as vibratory mills, ball mills and centrifugal mills.

A preferred blending apparatus comprises vibratory mills of the type described in pages 8-29 to 8-30 of Perry and Chilton's 5th edition of *Chemical Engineering Handbook*, McGraw-Hill Book Co.

An example of a preferred procedure for the practice of this invention, and of the fugitive binder product thereof, is as follows:

A charge of enriched uranium dioxide powder, granulated to a substantially uniform particle size, is deposited in a vibratory mill (Sweco Inc. Vibro-Energy mill) for blending with the binder forming ingredients. Solid ammonium oxalate in powder form is added to the uranium dioxide in an amount of about 0.8 percent based on the weight of the uranium dioxide. A water solution of about 48% by weight ethylenediamine carbamate is also added to the uranium dioxide in an amount providing about 1.63% by weight of water and about 1.5% by weight of solid ethylenediamine carbamate based on the weight of the uranium dioxide. The ratio of ammonium oxalate to the amine carbamate is about one part to 1.9 parts by weight. The combined ingredients are blended in the vibratory mill for a suitable period of about 25 minutes at a temperature of at least 65° C. to provide for their interaction to produce an effective fugitive binder comprising uranyl oxalate-carbonate.

The combined and interacted ingredients are dried and ammonia gas formed during the interaction is driven from the combined mass of ingredients by applying a heating gaseous medium at a temperature of not greater than about 150° C.

The product of the interaction of these ingredients as set forth above has been identified as uranyl oxalate-carbonate, having the formula:

$$[UO_2(CO_3)(C_2O_4).2H_2O].2H_2O.$$

A chemical analysis of two binder preparations according to the above procedure and ingredients is as follows:

|  | Batch 1 | Batch 2 |
|---|---|---|
| $H_2O$, ppm | 4958.0 | 5433.0 |
| $C_2O_4^=$ (oxalate) | 0.416% | 0.411% |
| $CO_2$ (carbonate) | 0.270% | 0.288% |
| U ($U^{+6}$) | 1.46% | 1.42% |

Molar ratios were determined to be:

| 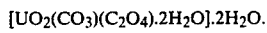 $U::C_2O_4^=::CO_3^=::H_2O$ | |
|---|---|
| Batch 1 | Batch 2 |
| 1::0.77::1::3.4 | 1::0.78::1.1::3.9 |

Infra-red spectra measurements confirm the above formulation.

What is claimed is:

1. A method of producing coherent compacts of particulate ceramic nuclear fuel which imparts enduring plasticity to the particulate ceramic material for extended processing, consisting essentially of the steps of:
   (a) adding a fugitive binder comprising a reaction product of a combination of at least one amine compound selected from the group consisting of carbonate or carbamate of ethylenediamine; monomethylene; 3,3 diaminodipropylamine; 1,3 diaminopropane; 1,6 diaminohexane; n butyl amine; diethylenetriamine; and 1,7 diaminoheptane with ammonium oxalate interacted at a temperature of at least about 65° C. and with uranium dioxide to particulate nuclear fuel material comprising uranium dioxide and blending the resulting binder product therethrough; and
   (b) pressing the resultant blend comprising particulate fuel material and binder into a coherent compact.

2. The method of claim 1, wherein the amine compound is in an aqueous solution when combined with the ammonium oxalate.

3. The method of claim 1, wherein the amine compound is ethylene diamine carbamate.

4. The method of claim 1, wherein the fugitive binder comprises a reaction product of uranium dioxide with a combination of about 0.5% to about 7% by weight of the amine compound and about 0.25% to about 4% by weight of ammonium oxalate based upon the weight of the particulate nuclear fuel material.

5. The method of claim 1, wherein the amine compound and ammonium oxalate ingredients of the fugitive binder are combined before being added to the uranium dioxide.

6. The method of claim 3, wherein the ethylene diamine carbamate is in aqueous solution and the ammonium oxalate is added as a powdered solid when combined.

7. The method of claim 3, wherein the ethylenediamine carbamate is in aqueous solution and the ammonium oxalate is dispersed in said aqueous solution of ethylenediamine carbamate before adding to the uranium dioxide.

8. The method of claim 3, wherein the fugitive binder comprises a reaction product of uranium dioxide with the product of the combination of about 0.5% to about 7% by weight of ethylenediamine carbamate and about 0.25% to about 4% by weight of ammonium oxalate based upon the weight of the particulate nuclear fuel material.

9. The method of claim 3, wherein the fugitive binder comprises a reaction product of uranium dioxide with the product of the combination of about 1.5% of weight of ethylenediamine carbamate and about 0.8% by weight of ammonium oxalate based upon the weight of the particulate nuclear fuel material.

10. A method of producing coherent compacts of particulate ceramic nuclear fuel which imparts plasticity to the particulate ceramic material for extended processing, consisting essentially of the steps of:

(a) preparing a fugitive binder comprising a reaction product of an amine compound selected from the group consisting of carbonate or carbamate of ethylenediamine; monomethylene; 3,3 diaminodipropylamine; 1,3 diaminopropane; 1,6 diaminohexane; n butyl amine; diethylenetriamine; and 1,7 diaminoheptane with ammonium oxalate interacted at a temperature of at least about 65° C. and with uranium dioxide for particulate nuclear fuel material by adding ammonium oxalate and an aqueous solution of the amine compound, in approximate ratios of about one part by weight of ammonium oxalate to about 1.9 parts by weight of the amine compound, to particulate ceramic nuclear fuel containing uranium dioxide; and (b) blending said added ingredients with the particulate nuclear fuel containing uranium dioxide to interact the ingredients and produce a binder for said particulate nuclear fuel.

11. The method of claim 10, wherein the blend of particulate nuclear fuel material comprising uranium dioxide binder with the fugitive binder is compressed into a coherent compact.

12. A compression moldable particulate mixture containing particulate ceramic nuclear fuel material consisting essentially of the combination of particulate ceramic nuclear fuel material including uranium dioxide and a fugitive binder composed of the interaction product of ammonium oxalate and at least one amine compound selected from the group consistng of carbonate or carbamate of ethylenediamine; monomethylene; 3,3 diaminodipropylamine; 1,3 diaminopropane; 1,6 diaminohexane; n butyl amine; diethylenetriamine; and 1,7 diaminoheptane in aqueous solution interacted at a temperature of at least about 65° C. and with uranium dioxide of the ceramic nuclear fuel material.

13. The compression moldable particulate mixture of claim 12, which has been compressed into coherent compacts.

14. A method of producing coherent compacts of particulate ceramic nuclear fuel which imparts enduring plasticity to the particulate ceramic material for extended processing, consisting essentially of the steps of:

(a) preparing a fugitive binder for particulate nuclear fuel material by adding ammonium oxalate and an aqueous solution of ethylenediamine carbamate, in approximate ratios of about one part by weight of ammonium oxalate to about 1.9 parts by weight of the ethylenediamine carbamate, to particulate ceramic nuclear fuel containing uranium dioxide;

(b) blending said added ingredients with the particulate nuclear fuel including uranium dioxide at a temperature of at least about 65° C. to interact the added ingredients and produce a binder reaction product with the uranium dioxide for said particulate nuclear fuel; and (c) drying the combined and interacted ingredients and removing water and ammonia gas from the combined mass by applying a heated gas the temperature of which is not greater than 150° C.

15. A method of producing coherent compacts of particulate ceramic nuclear fuel which imparts enduring plasticity to the particulate ceramic material for extended processing, consisting essentially of the steps of:

(a) adding a fugitive binder comprising a uranyl oxalate-carbonate reaction product of a combination of an amine compound selected from the group consisting of carbonate or carbamate of ethylenediamine; monomethylene; 3,3 diaminodipropylamine; 1,3 diaminopropane; n butyl amine; diethylenetriamine; and 1,7 diaminoheptane in solution and ammonium oxalate interacted at a temperature of at least about 65° C. with uranium dioxide to particulate nuclear fuel material containing uranium dioxide, and blending the resulting binder product therethrough; and (b) pressing the resultant blend comprising particulate fuel material and binder into a coherent compact.

16. The method of claim 15, wherein the uranyl oxalate-carbonate reaction product is prepared by combining the amine compound and ammonium oxalate with uranium dioxide and then adding said combined binder forming ingredients to the particulate nuclear fuel material.

17. The method of claim 15, wherein the uranyl oxalate-carbonate reaction product is prepared by adding the amine compound and ammonium oxalate to the particulate nuclear fuel material containing uranium dioxide.

18. A method of producing coherent compacts of particulate ceramic nuclear fuel which imparts enduring plasticity to the particulate ceramic material for extended processing, consisting essentially of the steps of:

(a) adding a fugitive binder comprising a uranyl oxalate-carbonate reaction product of a combination of an amine compound in solution selected from the group consisting of carbonate or carbamate of ethylenediamine; monomethylene; 3,3 diaminodipropylamine; 1,3 diaminopropane; 1,6 diaminohexane; n butyl amine; diethylenetriamine; and 1,7 diaminoheptane and ammonium oxalate interacted at a temperature of at least about 65° C. and with uranium dioxide and having the composition of $(UO_2(CO_3)(C_2O_4).2H_2O).2H_2O$ to particulate nuclear fuel material containing uranium dioxide, and blending the resulting binder reaction product therethrough; and (b) pressing the resultant blend comprising particulate fuel material and binder into a coherent compact.

19. The method of claim 18, wherein the uranyl oxalate-carbonate reaction product of $(UO_2(CO_3)(C_2O_4).2H_2O).2H_2O$ is prepared by combining the amine compound and ammonium oxalate with uranium dioxide and water and then adding said combined binder forming ingredients to the particulate nuclear fuel material.

20. The method of claim 18, wherein the uranyl oxalate-carbonate reaction product of $(UO_2(CO_3)(C_2O_4).2H_2O).2H_2O$ is prepared by adding the amine compound in solution and ammonium oxalate to the particulate nuclear fuel material containing uranium dioxide.

21. The method of claim 18, wherein the amine is ethylenediamine carbamate in aqueous solution.

* * * * *